United States Patent [19]

Bijl et al.

[11] Patent Number: 4,931,554

[45] Date of Patent: Jun. 5, 1990

[54] METHOD OF PREPARING A SOLID COMPOSITION OF LACTULOSE, AND COMPOSITION SO OBTAINED

[75] Inventors: Hugo Bijl; Sebastiaan J. W. Vroklage, both of Olst, Netherlands

[73] Assignee: Duphar International Research B.V., Weesp, Netherlands

[21] Appl. No.: 311,953

[22] Filed: Feb. 17, 1989

[30] Foreign Application Priority Data

Feb. 22, 1988 [NL] Netherlands ............... 8800431

[51] Int. Cl.$^5$ .................. C07H 1/00; A01N 43/04
[52] U.S. Cl. ........................... 536/124; 514/53; 514/892; 424/439
[58] Field of Search .............. 536/124; 514/53, 892; 424/439

[56] References Cited

U.S. PATENT DOCUMENTS 4,282,319 8/1981 Conrad .................... 435/99
4,605,646 8/1986 Bernardi ................... 514/53

Primary Examiner—Ronald W. Griffin
Assistant Examiner—Pamela S. Webber
Attorney, Agent, or Firm—Stevens, Davis, Miller & Mosher

[57] ABSTRACT

The invention relates to a method of preparing a solid composition of lactulose in a simple way. According to the invention lactulose syrup is mixed with Fiberform ®, i.e. a fibre product based on the husks of corn grains having a fibre content of more than 80%. The mixture is spread, dried, crushed and optionally sieved.

8 Claims, No Drawings

METHOD OF PREPARING A SOLID COMPOSITION OF LACTULOSE, AND COMPOSITION SO OBTAINED

The invention relates to a method of preparing a solid composition for the administration of lactulose and to the composition so obtained.

It is known that lactulose, an isomerisation product of lactose, is particularly suitable for the treatment of inter alia chronic constipation and hepatic coma. Usually lactulose in the form of a 50% solution of lactulose in water is used. However, the use of lactulose in the form of such a syrup is far from ideal.

Furthermore, the use of lactulose in a crystalline form is known. However, the crystallisation process of lactulose proceeds particular laborious.

Finally British patent application No. 2,156,196 relates to compositions of therapeutic or dietetic use comprising vegetable fibre and lactulose. The two components should demonstrate a strong reciprocal synergic effect. Vegetable fibre or dietetic fibre as used in this composition contain between 11 and 22% of fibre, known as "active" fibre of "raw fibre". by means of a number of other components this known composition may be processed in the form of dietetic products, in particular in the form of biscuits.

It is the object of the present invention to provide an easy method for the preparation of a solid composition for the administration of lactulose.

It has been found that a solid composition for the administration of lactulose can be obtained by providing lactulose syrup on a moisture-absorbing fibre product as a carrier for the lactulose syrup. Conventionally used carrier materials for liquid medicines, for example, aerosil, lactose and CaHPO$_4$ have proved to be unfit for this purpose.

Also vegetable fibrous materials (i.e. raw fibre) cannot be used as a moisture-absorbing carrier for the preparation of a solid composition for the administration of lactulose.

It has been found in particular that the diet fibre product based on the husks of corn grains, which has a fibre content of more than 80% by weight known as Fiberform ® can very well be used as a carrier material in order to prepare in a simple manner a suitable solid composition for the administration of lactulose from lactulose syrup. Fiberform is used as an agent to control the intestinal activity. It is a granulate of a conditioned fibre-concentrate, manufactured from wheat bran through a selective three-stage enzymatic fermentation process. In phase 1 (proteolysis) the protein content is reduced with proteinase. In phase 2 (starch digestion) the product is treated with amylase to remove practically all starch. In phase 3 (removal of phytic acid) the naturally present enzyme phytase is activated to break down and remove over 90% of the phytic acid, which is known to bind essential minerals like iron, zinc, calcium and magnesium. The resulting granulate is of a standardized, reproducible pharmaceutical quality.

The solid composition for the administration of lactulose according to the invention is obtained in a simple manner by mixing the lactulose syrup with the Fiberform carrier material, spreading the mixture, drying it, crushing it and optionally sieving it to the desired grain size.

The preferred starting material is syrup comprising approximately 50% of solid lactulose. A quantity of 150–350 g, in particular 200–300 g, of Fiberform is used per liter of this syrup. The mixture is mixed for a few minutes and spread on a stainless steel plate. After drying for a few hours at a temperature of 60°–90° C., preferably approximtely 80° C., the product thus obtained is crushed, for example, in an oscillating gradulator, and finally sieved, if so desired, to the desired grain size.

No other auxiliary substances are necessary for the preparation of the solid composition of lactulose according to the invention, which is an advantage for a pharmaceutical product.

It is very surprising that a solid composition for the administration of lactulose can be obtained in such a simple manner. EXAMPLE 7.5 kg of the diet fibre product Fiberform were mixed with 32 kg of lactulose solution (Duphalac ®) in a Collette mixer for 5 minutes. The mixture was distributed over 20 "closed" drying plates and dried for 6 hours with an inlet air of 100° C. After drying for 2 hours and 4 hours respectively the mass was loosened. The dried mass was crushed by means of a Frewitt granulator having a sieve grating of 1.5 mm.

We claim:

1. A process of preparing a solid composition of lactulose comprising the steps of mixing a lactulose syrup with spreading the mixture, drying mixture, and crushing the mixture. product having a fiber content of more than 80% by weight.

2. A process as claimed in claim 1, wherein a 50% lactulose syrup is mixed with a quantity of Fiberform in the ratio of 150–350 g per liter of lactulose syrup.

3. The process of claim 1 in which the crushed mixture is sieved.

4. A process as claimed in claim 1, wherein the step of mixing comprising mixing the lactulose syrup and Fiberform for a few minutes.

5. A process as claimed in claim 1, wherein the drying step is carried out at 80° C. for six hours.

6. A solid composition of lactulose and Fiberform obtained according to the process of any one of claims 3 and 1–5.

7. A process as claimed in claim 1, in which the drying step comprises drying 60°–90° C. for a few hours.

8. A process as claimed in claim 2, characterized in that 200–300 g of Fiberform are used per liter of lactulose syrup.

* * * * *

UNITED STATES PATENT AND TRADEMARK OFFICE
CERTIFICATE OF CORRECTION

PATENT NO. : 4,931,554

DATED : June 5, 1990

INVENTOR(S) : Hugo Bijl et al

It is certified that error appears in the above-identified patent and that said Letters Patent is hereby corrected as shown below:

Column 2, lines 35-39, Claim 1 should read as follows:

1. A process of preparing a solid composition of lactulose comprising the steps of mixing a lactulose syrup with product having a fiber content of more than 80% by weight, spreading the mixture, drying the mixture, and crushing the mixture.

Signed and Sealed this

Second Day of March, 1993

*Attest:*

STEPHEN G. KUNIN

*Attesting Officer*      *Acting Commissioner of Patents and Trademarks*